United States Patent [19]

Chalifoux

[11] Patent Number: 5,820,375

[45] Date of Patent: Oct. 13, 1998

[54] DENTAL POST HAVING CUTTING AND NON-CUTTING SURFACES

[75] Inventor: Paul R. Chalifoux, Wellesley, Mass.

[73] Assignee: Wellesley Research Associates, Inc., Wellesley, Mass.

[21] Appl. No.: 679,984

[22] Filed: Jul. 16, 1996

[51] Int. Cl.[6] .................................................... A61C 5/08
[52] U.S. Cl. ............................................................. 433/221
[58] Field of Search ................................... 433/220, 221, 433/224, 225

[56] References Cited

U.S. PATENT DOCUMENTS

| 1,589,994 | 6/1926 | Simmons | 433/221 |
|---|---|---|---|
| 1,612,227 | 12/1926 | Simmons | 433/221 |
| 4,479,783 | 10/1984 | Weissman | 433/221 |
| 4,729,736 | 3/1988 | Weissman | 433/221 |

FOREIGN PATENT DOCUMENTS

| 292422 | 2/1930 | Italy | 433/221 |
|---|---|---|---|
| 391683 | 5/1933 | United Kingdom | 433/221 |

*Primary Examiner*—Nicholas D. Lucchesi
*Attorney, Agent, or Firm*—Paul J. Cook

[57] ABSTRACT

A dental post is provided having an upper portion and a lower portion. The lower portion has cylindrical sections of differing diameters. Grooves formed on the section walls form cutting surfaces on the post and serve as vents for cement introduced into a canal of a tooth. The post functions both as a bur and as a dental post.

16 Claims, 8 Drawing Sheets

DENTAL POST HAVING CUTTING AND NON-CUTTING SURFACES

BACKGROUND OF THE INVENTION

This invention relates to a dental post having cutting surfaces and non-cutting surfaces. More particularly, this invention relates to a vented self-guiding dental post having cutting surfaces and non-cutting surfaces.

At the present time, a dental prosthesis structure is formed onto a tooth stub to replace missing dentition. In this procedure, a diseased or damaged top portion of a tooth is removed to form a tooth stub. A base for a dental post portion of the dental prosthetic structure is formed by drilling into the root canal portion of the tooth stub to form a bore into which the dental post can be inserted. Presently available dental posts include grooves on their surface which are designed to improve retention of the post within the tooth stub. Dental cement is employed in the bore in conjunction with the dental post to secure the post in the tooth stub. A portion of the post extends above the tooth stub upper surface so that a dental prosthesis formed on the tooth stub can be retained.

Preformed posts are posts which are premade to specific dimensions and are used with matching burs having cutting surfaces dimensioned to form a bore sized to accept and retain the preformed post. The preformed post is then positioned into the bore, cut to the appropriate length and then removed from the bore. Cement is spun into the root canal with a device referred to as a lenticula spiral, placed directly with a syringe and/or placed directly on the post. The post is placed in the canal and held in position until excess cement exudes from the tooth stub and the cement hardens. Most preformed posts require placing filling material around the top of the post to transfer strength from the post to the crown subsequently positioned on the post. This procedure is referred to as the core build up or post and core procedure.

There are many problems which are encountered when utilizing preformed posts. These include:

An inaccurate fit develops with present bur technology.

Potential for perforation of the root is great with present burs.

There is inadequate resistance to rotational forces on the post.

Root fracture caused by lateral stresses occurs.

There is weak transfer of strength from the post to the crown positioned on the post.

An accurately drilled bore in the tooth stub results in good proximity of the post to the canal walls with a thin cement layer to provide greater success in properly positioning the post. Generally, it is desirable to have a cement layer within a 5 to 20 micron thickness range to provide desired post retention in the bore. When tipping or vibrating of the bur occurs during root preparation, as often occurs with present drilling systems, the resultant bore is inaccurately sized. This undesirable result increases the failure rate of preformed post systems. When drilling a straight hole for a straight post in a curved canal or when drilling a hole which does not align with a canal, perforation of a root and loss of a tooth can result. All posts must resist normal rotational forces which occur during normal or abnormal functions if there is insufficient tooth structure to provide resistance to these forces. In general, preformed posts do not provide good stability against rotational force because they have a circular cross-section and therefore rotate easily when placed in a round hole such as is provided by present bur systems. Presently, to compensate for this, a separate pin may be placed into the tooth. Some post placement systems attempt to make posts oval or non-symmetrical at the post top. However, these post shapes do not supply dependable resistance and retention. The strength of the cement becomes a weak point to the root-post-crown relationship since excessively thick portions of the cement merely provide a suction force to hold the post in position. Constant repeated forces of chewing causes potential breakdown on the tooth-cement-crown interface with subsequent cement wash out and crown post failure. An uneven or excessive amount force can cause root fracture and tooth loss. In addition, forceful placement of cement type posts without proper venting of cement can cause root fracture and tooth loss. A filling material placed around a preformed post above the root to accept a crown after the post is cemented becomes a weak link in long term success of the crown. In addition, proper design of the post above the root is critical to resist rotation or dislodging of the filling material from the post.

A cast post is used for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these canal configurations. When utilizing a cast post, root preparation is done by drilling to remove undercuts and to obtain slight divergence from the bottom upward. In the cast post technique an impression of a prepared root canal space is taken. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing casts posts. The problems include:

An increased chance of root fracture. The cast post is expensive.

There is an increased possibility of root perforation.

The cast post may not provide good resistance to rotational forces.

All posts need to provide venting of cement as it is placed into a canal bore. A cast post is very precise fitting so it is difficult for cement to vent, lateral forces can fracture the root and/or the post will not be fully seated as excess cement remains in the bottom of the bore. In addition, any bubbles or inaccuracies from the casting process can cause a poor fit which results in root fracture. Cast posts are much more expensive than preformed posts because of laboratory fees and increased time required to treat the patient. For a cast post, an appointment is needed to form an impression in addition to an appointment for post placement. The patient cost of a cast post is about double the cost of a preformed post. The doctor's laboratory cost may be five to ten times the cost of a preformed post.

Preparation of a root canal space must be free of any undercuts. Otherwise, removal of a cast post in its plastic or wax phase of construction would be impossible. It is often difficult to avoid undercuts since root canals tend to be complex systems of lateral canals, ribbon shapes, multiple canals, etc. Therefore, excessive drilling often is required which effects removal of important tooth structure, resulting in a weaker root and increased chance of root fracture or perforation.

Present posts also are further classified as being parallel or tapered. Parallel posts have their sides parallel to each other. They form the strongest retention of any post design because the suction force created when they are placed into the tooth is strong. However, because they are parallel and have the same diameter through their length while root canal spaces are tapered, it is necessary to destroy more tooth structure as compared to a post having a tapered design. Tapered posts have sides angled relative to each other such that the bottom of the post has the smallest diameter. While tapered posts provide less retention forces as compared to parallel posts, more tooth structure is maintained with a tapered post which results in a stronger root. Unfortunately, tapered posts produce a wedging force when force is applied on the top of the post thereby resulting in increased root fracture.

British Patent 361,315 discloses a dental post having a stepped diameter construction and a cement vent. The post is used in conjunction with a burr having a shape similar to that of the post. The burr is provided only with cutting surfaces contacting the wall of the root canal.

U.S. Pat. Nos. 5,066,230 and 4,990,088 disclose a dental tool which functions as both a dental post and a burr for forming a bore in a tooth stub. The tool comprises a shaft having alternating surface areas along its length which are either a 100% cutting surface area contacting a root canal wall (or a 100% non-cutting surface area contacting a root canal wall.)

U.S. Pat. No. 5,145,373 discloses a dental post having a spiral groove along its length. The groove functions as a cement vent, a means for retaining the post in the root canal and as a threading means to aid in post removal in the event removal is necessary.

Accordingly, it would be desirable to provide a dental post which can be inserted into the bore of a tooth stub while maintaining maximum amount of tooth structure. It also would be desirable to provide such a post which is capable of cutting a tooth canal wall while eliminating the need for a separate burr. It also would be desirable to provide such a dental post which also minimizes or eliminates a wedging force during normal use of the tooth which force is normally present with presently available tapered posts. It would also be desirable to provide such a post which provides high retentive strength such as is obtained with dental posts having parallel sides. It also would be desirable to provide a post which provides accurate cutting and which permits cement venting.

SUMMARY OF THE INVENTION

This invention provides a dental post having an upper stem portion and a lower portion. The stem portion extends above a top surface of a tooth stub after the post is positioned within the tooth stub. The lower portion is positioned within the tooth stub after post placement.

The lower portion has parallel side surfaces and is formed of multiple sections having differing diameters. At least one section of the multiple sections has a surface which either is completely non-cutting or has a sufficiently large surface area which is non-cutting so that it functions as a guide for the lower portion to cause it to traverse the tooth bore path rather than directing the post through a wall of the bore. This section which functions on the guide is referred to herein as the non-cutting section. When the non-cutting section includes cutting surfaces, cutting is only effected by the non-cutting section when excessive lateral force is applied to the post by the user. Providing this non-cutting section, prevents passage of the post through the bore wall. The remaining sections of the lower portion provide the primary function of limited cutting of the tooth bore. Since the sides of the sections are parallel, little or no wedging force is exerted on the tooth as compared to a bur or post which is characterized by converging sides with the smallest diameter being at the bottom of the lower section and the largest diameter being at the top of the lower section.

The non-cutting section of the lower portion can be the top section, bottom section or positioned at an intermediate section of the lower portion. It is preferable to position the non-cutting section at the lowest section of the post. The term "non-cutting" surface as used herein refers to the solid outside surface of each section but excluding the cutting edges. Each section of the lower portion is formed from a cylindrical section having at least one portion comprising an open space that extends the length of the cylindrical section. The edges defining a line of demarcation between the space and the solid cylindrical section comprise the cutting surfaces. The primary cutting surfaces are positioned at the bottom of each section where the space, lower surface of the section and the cylindrical wall converge. Each segment removes only a small portion of the bore wall. Thus, the cutting function is distributed over all of the sections of the lower portion. By distributing the cutting forces rather than concentrating the cutting forces trauma to the root is minimized.

Since the tooth bore produced after the dentin is removed usually has tapered side walls with the smallest diameter being at the bore bottom and the largest diameter being at the bore top, when the multisection post is first inserted into the bore, the non-cutting section will immediately contact the bore wall or will contact the bore wall shortly after cutting is initiated. The effective post taper defined by a tangent line to the lower portion of the post matches or closely approximates the normal or prepared taper of a canal. For example, the cutting surfaces do not engage the canal walls until the post extends about 80% down the canal when the lower portion is divided into five equal heights. Cylinders contact with a lower portion having fewer cylinders occurs prior to this 80% extension while contact with more cylinders occurs at greater than about 80% extension. This is because the non-cutting section is sized to a diameter normally encountered in a tooth bore at the bore height where the non-cutting section is positioned.

For convenience, this invention will be described specifically hereinafter with regard to the preferred embodiment of this invention wherein the non-cutting section is positioned at the lowest position of the lower portion. This embodiment is preferred since the guiding function of the non-cutting section is effected immediately when the post is inserted into the tooth bore when it is desired to shape the tooth bore but cutting its walls to a shape which conforms to the shape of the post. However, it is to be understood that the non-cutting section can be positioned at any portion along the length of the lower section. The length of the non-cutting section generally comprises between about 1 and 50%, preferably between about 10 and 25% of the lower portion length.

In the preferred embodiment, the lowest section of the lower portion has the highest portion comprising non-cutting surface area. The portion of each section comprising the non-cutting surface area decreases from the lowest section to the highest section of the lower portion. The change in the ratio can be continuous or step-wise wherein each of a plurality of portions of the lower section has a constant ratio of non-cutting surface area to cutting surface area. As used herein, the term stepwise means that the ratio is constant for a short length of the lower section and then charges to a different ratio at a second short length of the lower section. That is, the ratio changes in steps each having a short length along the total length of the lower section.

The lowest section of the lower portion effects a small amount of cutting or no cutting while functioning primarily as a guide through the preexisting tooth bore as a result of the contact between the non-cutting surface and the bore wall. Each succeeding section of the lower portion above the lowest potion provides additional cutting of the bore wall so that the final cut bore has essentially the same shape as the lower portion of the post to be positioned within the bore.

The cutting surfaces are formed from one or more grooves extending into the post. In use, the tooth stub is first treated with a conventional endodontic fixes or reamers, Gates glidden, peeso reamer or the like to remove dentin from the canal extending into the tooth thereby to form a bore having an irregular wall surface. The dental post of this invention then is inserted into the formed canal and rotated to effect cutting of the canal wall and guidance of the post through the canal rather than through the outer wall of the tooth stub. The resultant bore conforms to the shape of the outer surface of the lower portion of the post so that it is tightly fit into the bore. The post is removed from the bore which is then washed to remove debris. Cement is then introduced into the bore. The post is then placed into the bore and excess cement exudes from the bore through spaces between the cutting surfaces. A top portion of the post is removed such as by cutting or removing a press-fit top section so that a crown or the like can be positioned on the exposed top portion of the post.

BRIEF DESCRIPTION OF THE DRAWINGS

FIG. 7b illustrates the shape of the tooth bore after cutting with the post of FIG. 7a.

DESCRIPTION OF SPECIFIC EMBODIMENTS

The dental post of this invention includes an upper stem portion for attachment of a dental prosthesis and a lower portion. The lowest portion functions (a) as a guide to position the post within a tooth canal or bore, (b) as a bur to shape the dental canal to conform to the outer surface of the post and (c) as a dental post to support the upper stem portion in a desired position on the tooth. A lowermost section of the lower portion either has no cutting surface or has the highest portion of its surface area being non-cutting surface. This lowermost section functions to guide the post within the tooth canal from which dentin has been removed rather than guiding the post through a wall of the canal. The lower portion of the post has a decreased portion of its circumference functioning as a cutting surface rather than a non-cutting surface in a direction beginning from the lowermost section and extending to the uppermost section of the lower portion.

The open space between the cutting surfaces on the post function as a vent for cement within the canal after cement has been placed therein and the post is subsequently inserted into the canal. Since the lowermost section of the post functions to guide the post through the canal and the cutting surfaces cut into the walls of the canal to conform the canal shape to the outer surface shape of the lower portion of the post, the space between the post and the tooth canal can be maintained within a desired range of about 1 micron to about 200 microns, preferably between about 5 microns to about 40 microns so that the desired cement thickness between the wall and post can be attained. The width of this space can be easily controlled by minimizing moving the post gently from side to side during post rotation when cutting the canal walls. Cement thickness is an important factor to control successful post function. If cement is too thick, side forces on the top portion of the post transfer compressive force on the cement which leads to cement failure. Thin cement layer prevent of minimize compressive force on the cement.

Subsequent to cutting, the canal is cleared of debris such as with a water stream and cement is then inserted therein. Finally, the post is reinserted into the canal without a rotational force that would cause cutting and excess cement is vented from the canal through the space between the cutting surfaces.

As set forth above, the dental post of this invention includes an upper portion and a lower portion. The upper portion is designed in any conventional manner to include flanges, through splits, matching cores, wings, irregular shapes or the like. The lower portion is designed to have at least two sections. The effective diameter of the subsections decreases in the vertical direction away from upper portion. That is, the effective diameter of a given section is less than the effective diameter of all the sections above it. The result of having the effective section diameter decrease in the vertical direction away from the upper portion is that the lower portion tapers inwardly and avoids a wedging effect on the tooth bore wall. Decreasing the effective diameter of the lower portion of the post allows for conservation of more tooth structure, greater root strength and, therefore, less chance of root fracture and tooth loss. The sections of the lower portion of the post are shaped so that the lowermost section has a diameter larger than a diameter of a bottom of a root canal subsection below it. This permits the post section to rest on a step of the root canal subsection rather than being positioned to exert a wedging force when downward force is exerted on the post. When the lower most section bypasses a step, it will exert a wedging force during use. Thus, for example, a section having a conical section with the apex of the section being the lowermost and the base of the section being the uppermost portion is not useful herein. Such a subsection would exert a wedging action during use since the post would be forced downwardly thus subjecting the step to an increased diameter portion of the post.

This invention also provides for posts having other features conventionally used on posts including extensions, cutting extensions, threads, interrupted threads, through slots, venting slots, indentations, a disk at the top of the post which is positioned on the top of a tooth, used with indentations created in the root canal walls, or the like.

Referring to FIGS. 1, 1a, 1b, 1c, 1d, 1e, 1f and 1g, the post 10 includes an upper portion 12 positioned above dotted line 14 and a lower portion 16 positioned below dotted line 14. The lowermost section 18 of lower portion 16 includes cutting surfaces 19, 20, 21 and 22 and has the highest proportion of the surface area comprising non-cutting surfaces 23 and 24 since the spaces 25 and 26 between the cutting surfaces are small. The lowermost section 18 also can have no cutting surfaces and it functions to guide the post 10 through a tooth canal rather than into a wall of the canal. The proportion of the surface of the post sections 27, 28, 29, 30, 31 and 32 comprising non-cutting surfaces 33, 34, 35, 36, 37 and 38 decrease when moving in a direction toward the uppermost section 32 of lower portion 16. In addition, the diameter of the post sections progressively increase from post section 18 to post section 32. By providing progressively larger post sections in this manner, the lower portion 16 can be snugly fit into the tapered canal which is also cut into the shape of the lower portion 16 when the post 10 is rotated within the canal to effect canal wall cutting. In addition, since the walls of the post sections are parallel rather than tapered, the post positioned within the canal does not exert a wedging force on the canal walls. The final canal shape will have a shape which conforms to the outer shape of section 16.

Figure 1:
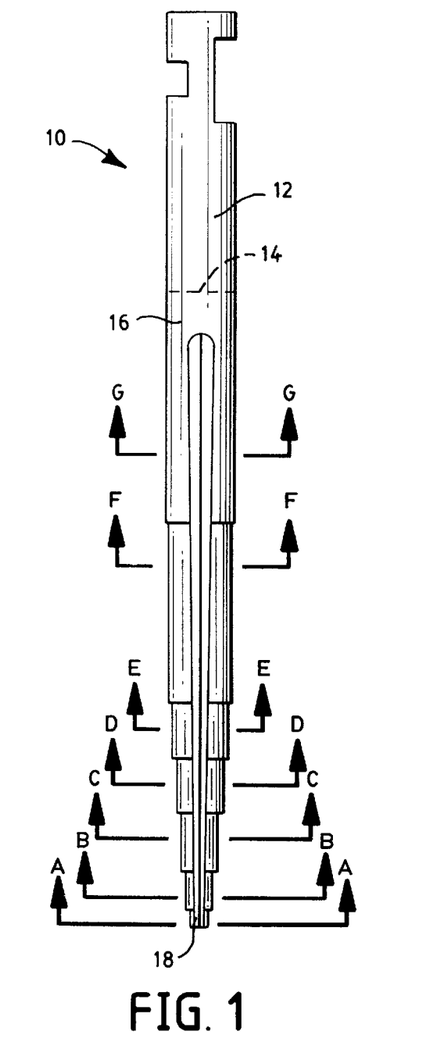
FIG. 1 is a side view of a dental post of this invention.
Figure 1A:
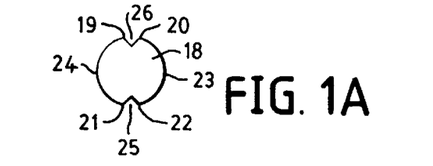
FIG. 1a is a cross-sectional view of FIG. 1 taken along line a—a.
Figure 1B:
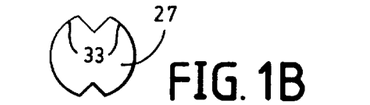
FIG. 1b is a cross-sectional view of FIG. 1 taken along line b—b.
Figure 1C:
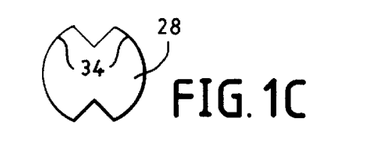
FIG. 1c is a cross-sectional view of FIG. 1 taken along line c—c.
Figure 1D:
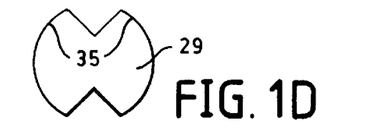
FIG. 1d is a cross-sectional view of FIG. 1 taken along line d—d.
Figure 1E:
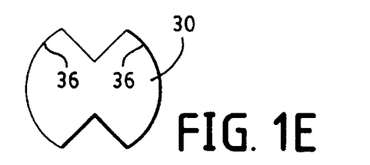
FIG. 1e is a cross-sectional view of FIG. 1 taken along line e—e.
Figure 1F:
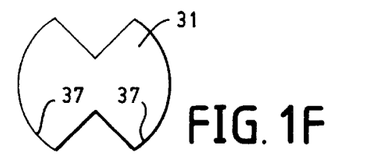
FIG. 1f is a cross-sectional view of FIG. 1 taken along line f—f.
Figure 1G:
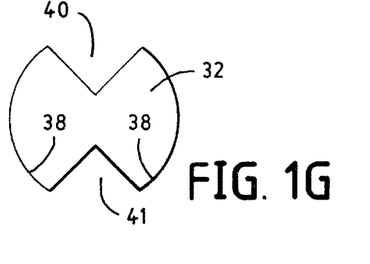
FIG. 1g is a cross-sectional view of FIG. 1 taken along line g—g.
Figure 2:
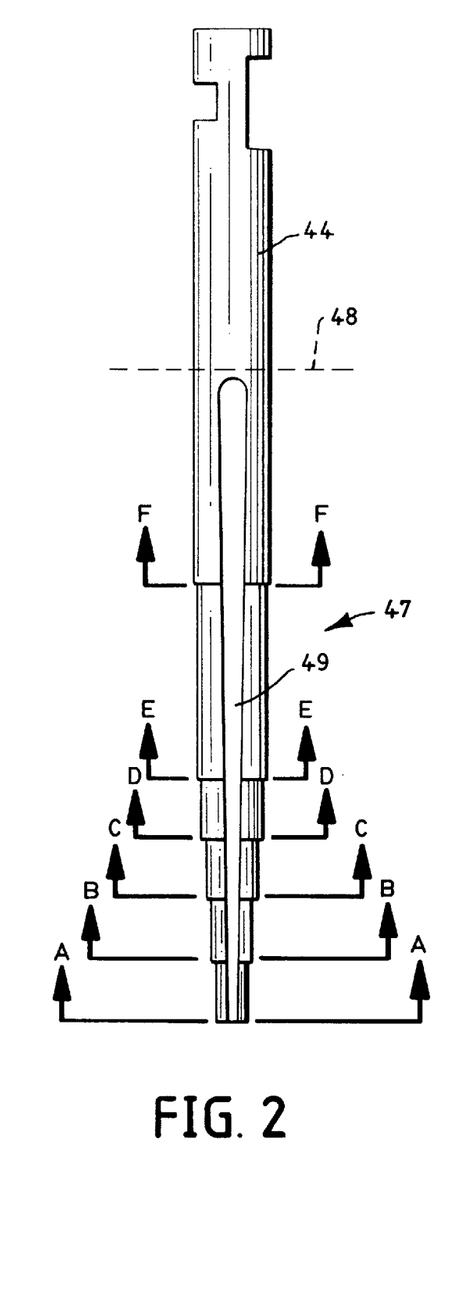
FIG. 2 is a side view of a post of this invention having a lower section with a constant diameter.
Figure 2A:
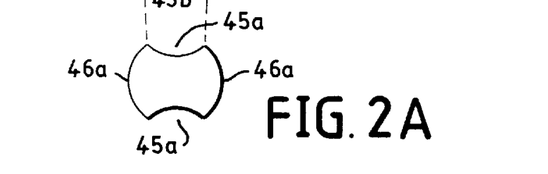
FIG. 2a is a cross-section of the post of FIG. 2 taken along line a—a.
Figures 2B, 2C:
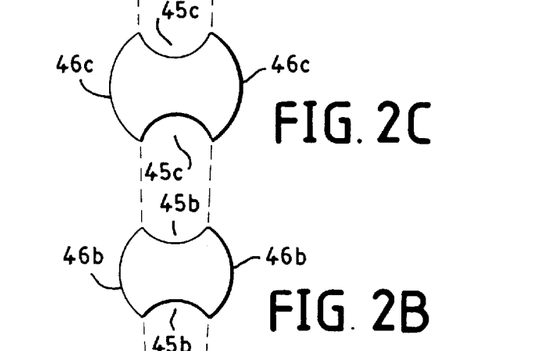
FIG. 2b is a cross-section of the post of FIG. 2 taken along line b—b.
FIG. 2c is a cross-section of the post of FIG. 2 taken along line c—c.
Figure 2D:
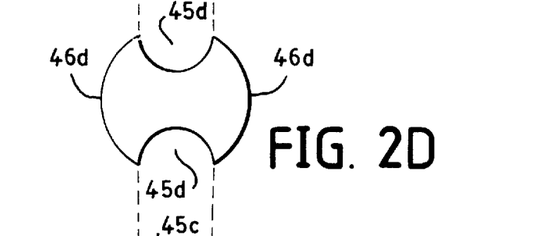
FIG. 2d, is a cross-section of the post of FIG. 2 taken along line d—d.
Figure 2E:
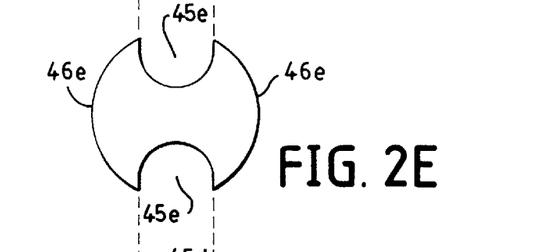
FIG. 2e, is a cross-section of the post of FIG. 2 taken along line e—e.
Figure 2F:
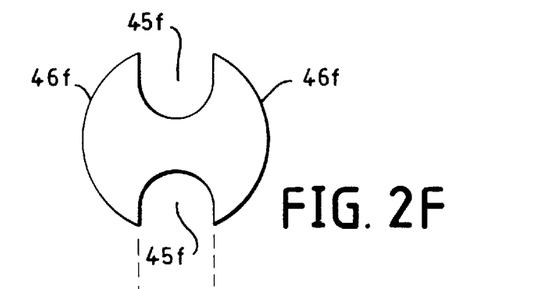
FIG. 2f, is a cross-section of the post of FIG. 2 taken along line f—f.

After cutting the canal, the post 10 is removed from the canal which is then washed to remove debris therefrom. Cement is inserted into the canal and the lower section 16 then is inserted into the canal. Excess cement is vented from the canal through spaces 25 and 26, through the spaces in intervening sections 27, 28, 29, 30 and 31 and lastly through spaces 40 and 41 in the uppermost section 32. Thus, the post 10 functions as a bur, a post and a vent for excess cement.

In addition, the post provides a means for shaping the tooth canal to precisely conform to the outer shape of the lower section 16 of the post 10. The post eliminates the need for a separate bur, insures precise formation of a canal shape which accommodates the post and provides a means for venting excess cement. The provision of a bur, post and cement means in a single dental apparatus not only significantly reduces the needed apparatus for implementing the post but also significantly reduces the time needed for subjecting a patient to a procedure for building a prosthesis on a tooth stub.

Referring to FIGS. 2, 2a, 2b, 2c, 2d, 2e and 2f, an alternative dental post construction of this invention is illustrated. Post 44 is provided with uniform width space 49 subdivided into spaces 45a, 45b, 45c, 45e and 45f between non-cutting surfaces 46a, 46b, 46c, 46d, 46e and 46f in the lower section 47 below line 48. The diameter of each subsection progressively increase from section a—a to section f—f such that uniform space 49 results in an increase in the ratio of non-cutting surface to total circumference from section a—a to f—f. The result of increased ratio of non-cutting to total circumference is that section f—f provides the most guidance for root canal wall preparation. In use, post 44 is placed into a tapered canal such that sections a—a, b—b, c—c, d—d, e—e, and f—f of lower section 47 of post 44 all engage tooth structure at approximately the same time and guidance for the direction of root canal wall preparation is provided by the upper most section f—f. The uniform space 49 provides final excess cement venting when the post is inserted.

Figure 3A:
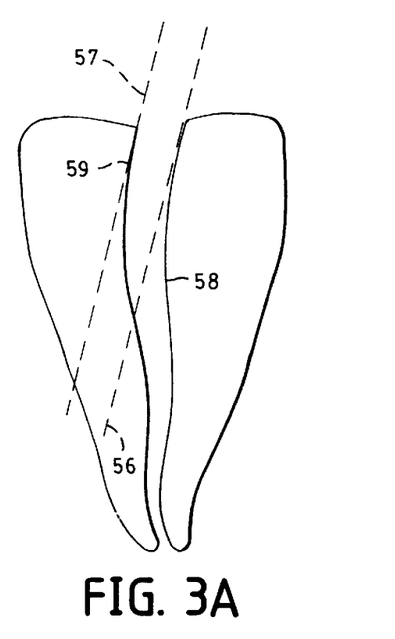
FIG. 3a illustrates a common result obtained with a bur of the prior art.
Figure 3B:
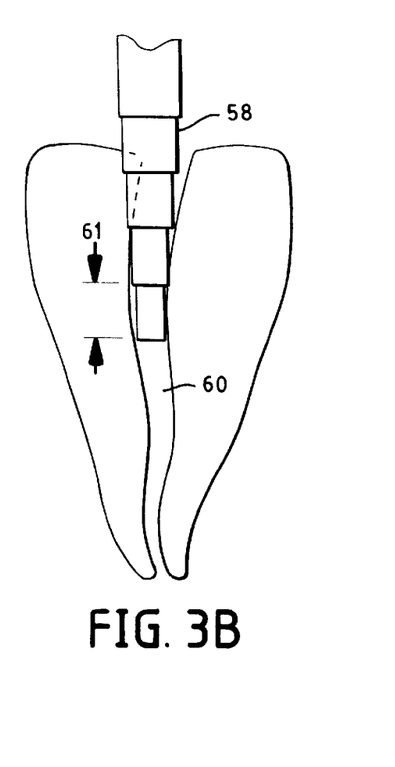
FIG. 3b illustrates the result obtained with the dental post of this invention.

FIG. 3a illustrates a common result which occurs without the guiding function of the post of this invention. When excess cutting surfaces are provided at the lower portion 56 of a post or bur 57, the post or bur 57 will not follow the path of tooth canal 58 but will pass through wall 59 of tooth canal 58 to insure incorrect positioning of post 57. In contrast, as shown in FIG. 3b, the post 58 of this invention will follow the path defined by the canal 60 since the leading section 61 of the post 58 follows the path defined by canal 60 rather than passing through a canal wall as shown in FIG. 3a.

Figure 4A:
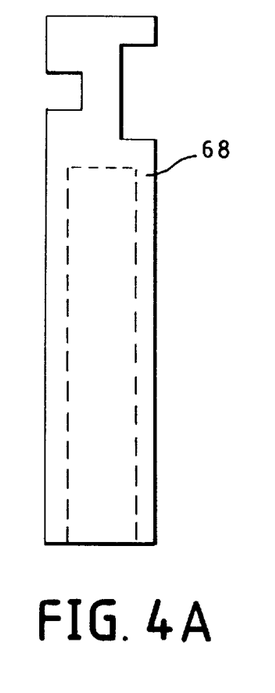
FIG. 4 is a cross-sectional view of a dental post of this invention.
Figure 4B:
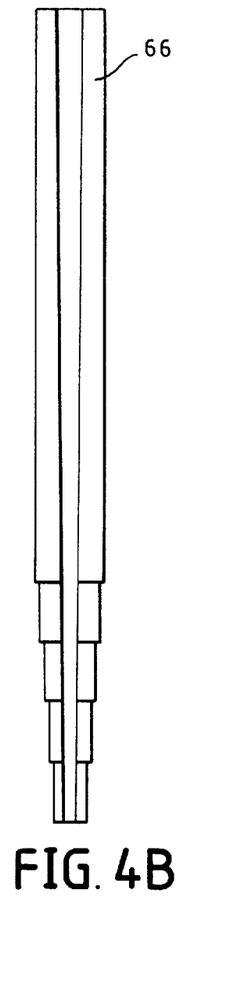
Figure 4C:
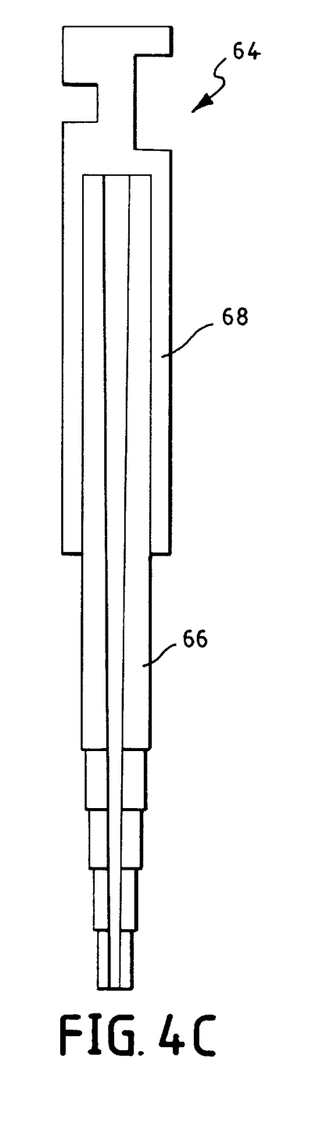

Referring to FIGS. 4a, 4b and 4c, a two piece dental post bur of this invention is illustrated. The post 64 includes a lower portion 66 having essentially the same configuration as shown in FIG. 1 and a top section 68. After the desired canal configuration has been formed by rotating the lower portion 66 in a tooth canal substantially free of dentin, the top section 68 is separated from lower portion 66 and lower portion 66 is implanted into a tooth canal as set forth above.

Figure 5:
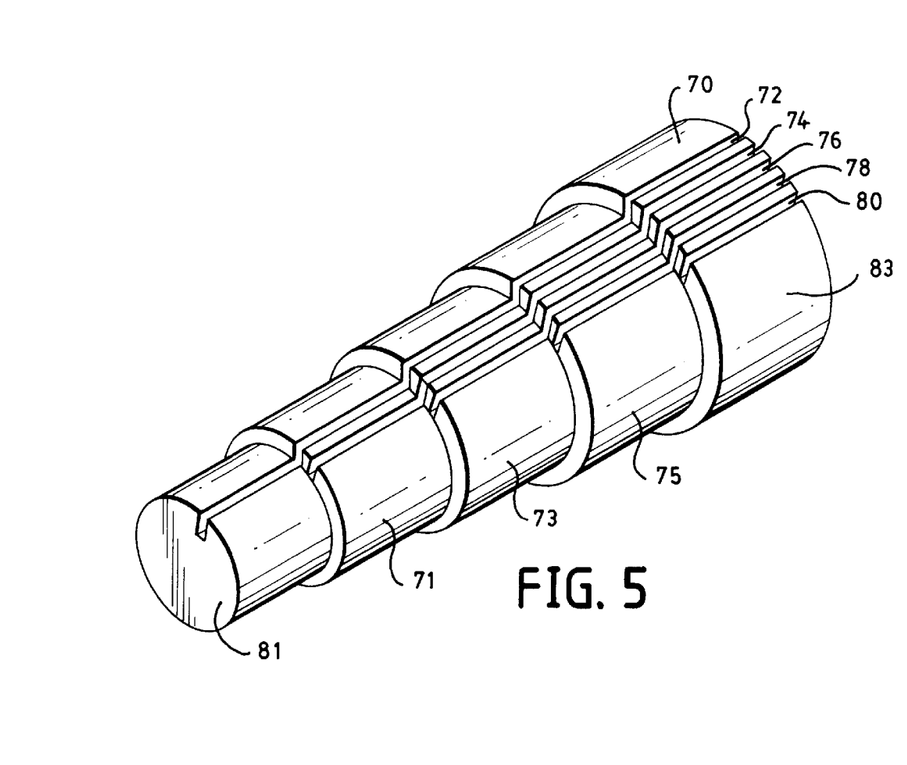
FIG. 5 is a perpendicular view of an alternative dental post of this invention.

Referring to FIG. 5, an alternative embodiment of this invention is illustrated wherein a progressively increasing number of vents are shown to increase the number of cutting surfaces progressively from the lowermost section 81 to the uppermost section 83 of the lower portion of the post to effect the results set forth above. As shown in FIG. 5, the number of cutting surfaces along the length of the lower portion 70 of a post of this invention is increased by increasing the number of vents 72, 74, 76, 78 and 80 when progressing from the lower-most section 81 to the uppermost portion 83 of lower portion 70. The progressively increased number of cutting surfaces effectively decreases the non-cutting surface areas as the progression is made from lowermost section 81 to uppermost section 83. The essential feature is that the non-cutting surface area decreases from the lowermost section 81 to the uppermost section 83 of the lower portion 70 to effect the desired results set forth above. That is, the lower-most section 81 functions primarily as a guide while the upper-most section 83 functions primarily as a cutting section and the intermediate sections 71, 73 and 75 also function primarily as cutting sections.

Figure 6:
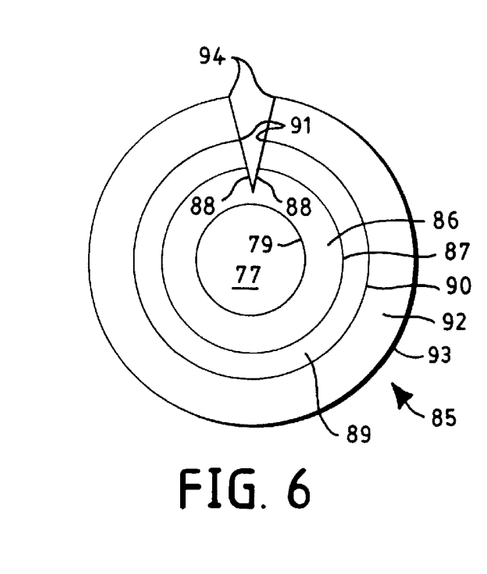
FIG. 6 is a bottom view of a dental post of this invention of the type shown in FIG. 1 but having four sections..

Referring to FIG. 6, the post 85 includes a lowermost section 77 including 100% of its surface 79 as a non-cutting surface. The lower intermediate section 86 has the lowest cutting surfaces area 88. The higher intermediate section 89 has a higher cutting surface area 91 than section 86. The uppermost section 92 has the highest cutting surfaces area 94.

Figure 7A:
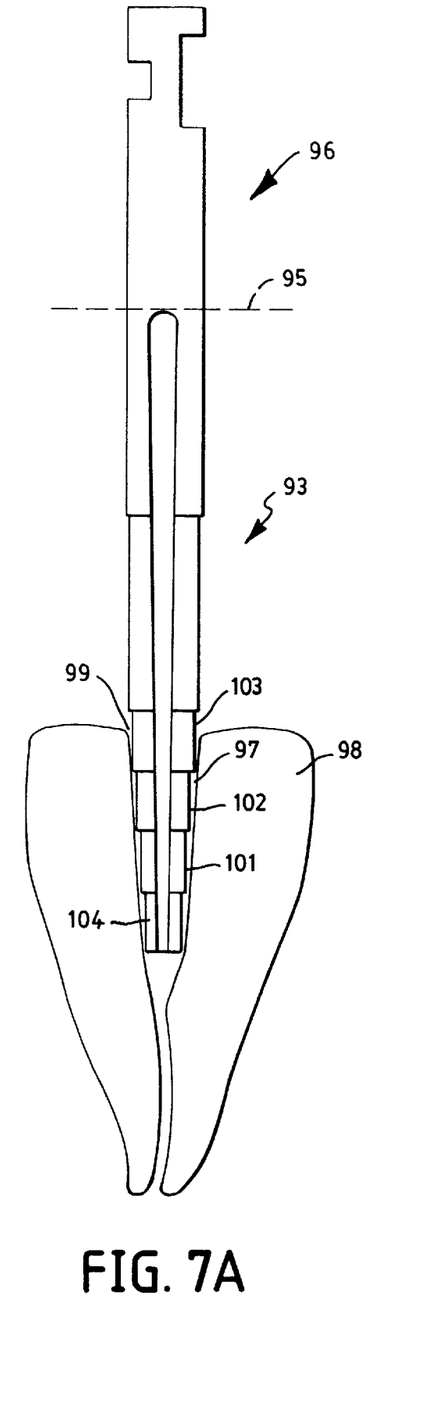
FIG. 7a illustrates the initial engagement of the post of FIG. 1 to a tooth bore wall.
Figure 7B:
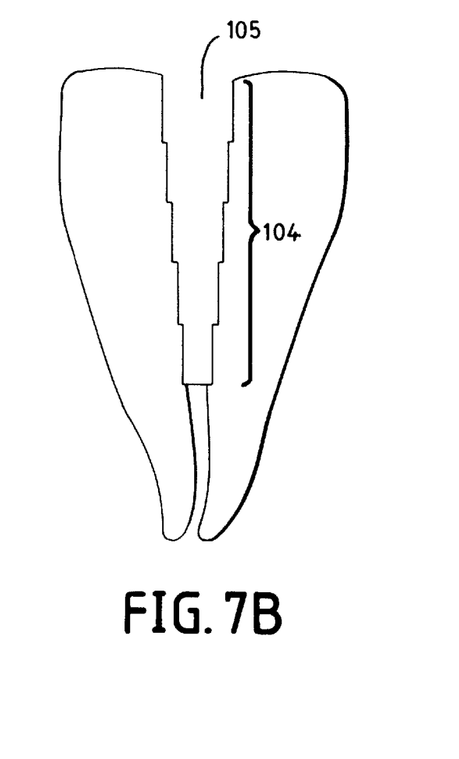

FIG. 7a illustrates that a large proportion of the lower portion 93 of post 96 below line 95 is positioned within canal 97 of tooth 98 before contact is made between the lower portion 93 and the canal wall 99. Thus, the intermediate section 101, 102 and 103 can contact the wall 99 to effect cutting rather than being dependent upon lowermost section to complete its cutting function prior to their effecting the cutting function. The final shape of the cut canal wall 104 which provides an excellent fit for positioning the majority of the length of lower portion 93 of post 96 into the canal 105 so that only a thin layer of cement is required between the wall 104 and the lower portion 93.

Figure 8:
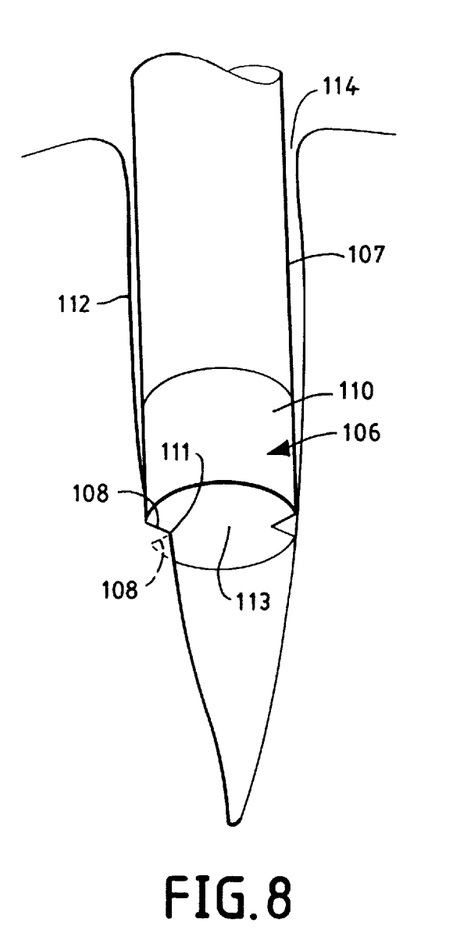
FIGS. 8, 8a and 8b illustrate the cutting function of the post of this invention.
Figure 8A:
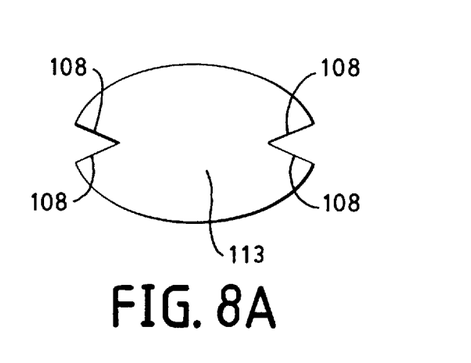
Figure 8B:
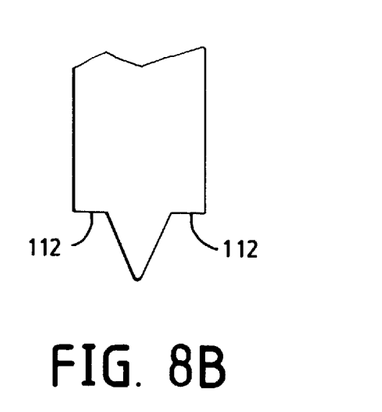

The limited penetration of the post of this invention into a canal wall is illustrated in FIGS. 8, 8*a* and 8*b*. The lowermost section 106 of post 107 includes cutting surfaces 108 having a depth extending from the outer surface 110 of section 106 to apex 111. This cutting surface configuration limits the depth into the canal wall 112 to which section 106 can extend. The bottom non-cutting surface 113 provides a stop means for the post 107 to limit the depth the post 107 extends into canal 114.

Figure 9:
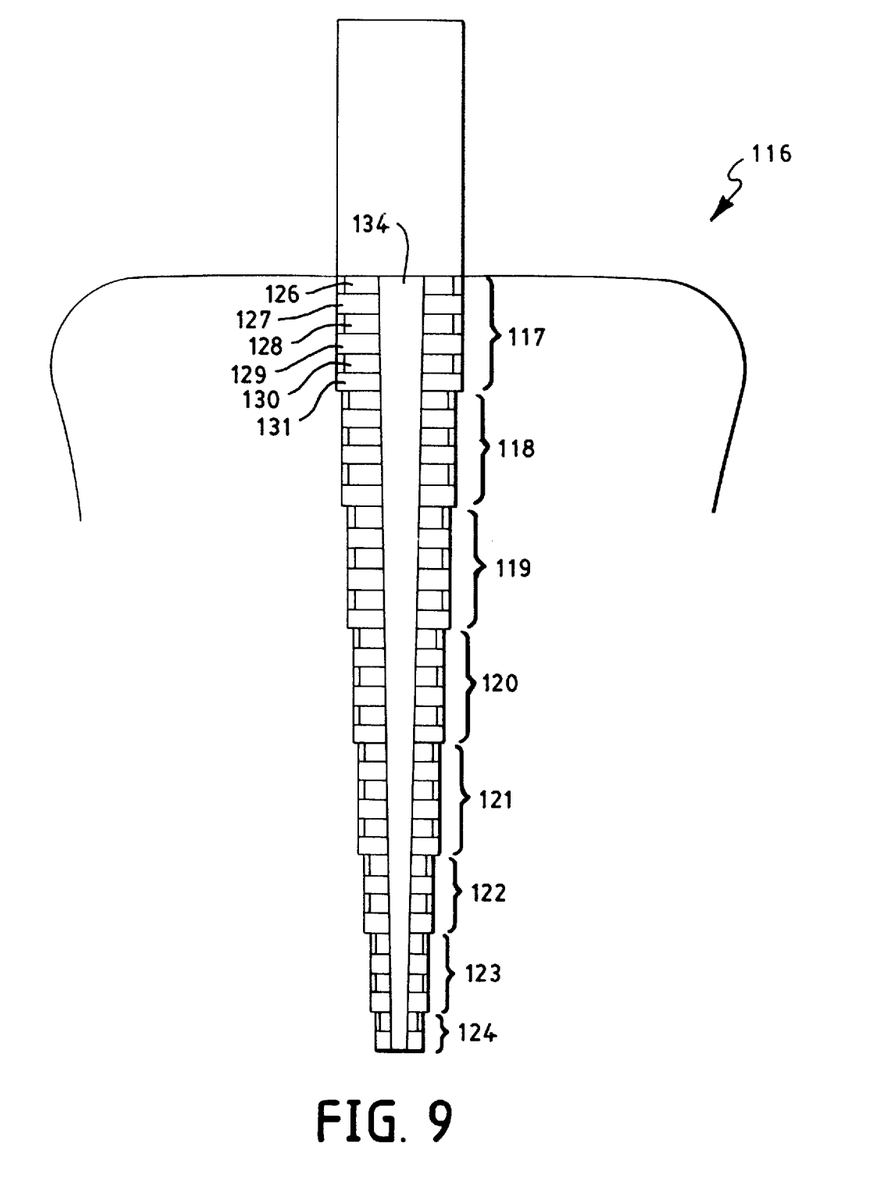
FIG. 9 illustrates an alternative post of the invention.

Referring to FIG. 9, the post 116 is provided with a plurality of sections 117, 118, 119, 120, 121, 122, 123 and 124. Each section is provided with a plurality of subsections such as subsection 126, 127, 1228, 129, 130 and 131. The subsections 127, 129 and 131 define the area of the non-cutting surface. The slot 134 which extends the length of the lowest portion of 116 forms the cutting surface along the post length. By segmenting each section in this manner an increased measure of control of non-cutting surface is provided.

I claim:

1. A dental post shaped to fit into a canal of a tooth, which comprises:

a top portion, a bottom portion connected to said top portion and positioned to extend into said canal, said bottom portion formed from a plurality of generally cylindrical sections each having a diameter different from remaining sections, a lowermost section of said plurality of sections having a smallest section diameter being the section most remote from said top portion, an uppermost section of said sections having a largest section diameter being the section in closest proximity to said top portion, wherein sections positioned between said lowermost section and said uppermost section having progressively larger diameters in a direction from said lowermost section to said uppermost section, said plurality of sections, optionally including said lowermost section, having means for cutting a wall of said canal when said post is rotated within said canal, said means comprising at least one groove in a wall portion of said sections which defines cutting edges, the remaining portion of said wall, excluding said at least one groove being a non-cutting surface, at least one of said plurality of sections, having a sufficiently large non-cutting surface area to function primarily as a guide through the canal when said post is rotated in contact with said wall of said canal.

2. The post of claim 1 wherein said lowermost section includes at least one groove which defines cutting edges.

3. The post of claim 1 wherein said lowermost section is free of grooves.

4. The dental post of claim 1 wherein said lowermost section functions primarily as said guide.

5. The dental post of claim 1 wherein said uppermost section functions primarily as said guide.

6. The dental post of claim 1 wherein a section intermediate said lowermost section and said uppermost section functions primarily as said guide.

7. The dental post of claim 1 wherein a plurality of said sections are formed of at least two sub sections, each having a diameter different from at least one other subsection.

8. The post of claim 1 wherein the sections and optionally the lowermost section includes two grooves.

9. The process of positioning a dental post within a tooth which comprises:

removing dentin from a canal of a tooth, positioning into said canal a post comprising: a top portion, a bottom portion connected to said top portion, and positioned to extend into said canal, said bottom portion formed from a plurality of generally cylindrical sections each having a diameter different from remaining sections, a lowermost section of said plurality of sections having a smallest section diameter being the section most remote from said top portion, an uppermost section of said sections having a largest section diameter being the section in closest proximity to said top portion, wherein sections positioned between said lowermost section and said uppermost section having progressively larger diameters in a direction from said lowermost section to said uppermost section, said plurality of sections optionally including said lowermost section having means for cutting a wall of said canal when said post is rotated within said canal, said means comprising at least one groove in a wall portion of said sections which defines cutting edges, the remaining portion of said wall, excluding said at least one groove being a non-cutting surface, at least one of said plurality of sections, having a sufficiently large non-cutting surface area to function primarily as a guide through the canal when said post is rotated in contact with said wall of said canal, rotating or oscillating said post within said canal to form a shaped canal shaped into a form approximately the outer surface shape of said lower portion, removing said post from said shaped canal, adding cement into said shaped canal and, reinserting said post into said shaped canal.

10. The process of claim 9 wherein said lowermost section of said post includes at least one groove which defines cutting edges.

11. The process of claim 9 wherein said lowermost section of said post is free of grooves.

12. The process of claim 9 wherein said lowermost section of said post functions primarily as said guide.

13. The process of claim 9 wherein said uppermost section of said post functions primarily as a guide.

14. The process of claim 9 wherein a section of said post intermediate said lowermost section and said uppermost section functions primarily as said guide.

15. The process of claim 9 wherein a plurality of said sections of said post are formed of at least two subsections each having a diameter different from at least one other subsection.

16. The process of claim 9 wherein a plurality of said post and optionally said lowermost section includes two of said grooves.

* * * * *